(12) United States Patent
Kim et al.

(10) Patent No.: US 6,485,712 B1
(45) Date of Patent: Nov. 26, 2002

(54) UV BLOCKING AND SLIMMING COSMETIC COMPOSITION

(75) Inventors: Won Kyu Kim, Bangebae Pine Villa #101, 12-11, Bangbae bon-dong, Seocho-gu, Seoul (KR); Kye Won Lee, Kyunggi-do (KR); Sun Jung Lee, Kyunggi-do (KR); Bong Jun Kim, Kyunggi-do (KR); Hye Young Lee, Choongcheongbuk-do (KR); Chul Hong Park, Pusan-si (KR); Dong Soo Kim, Kyunggi-do (KR); Kyeong Bum Choi, Seoul (KR); Eun Joung Yoo, Kyunggi-do (KR)

(73) Assignee: Won Kyu Kim, Seoul (KR)

( * ) Notice: Subject to any disclaimer, the term of this patent is extended or adjusted under 35 U.S.C. 154(b) by 0 days.

(21) Appl. No.: 10/035,233

(22) Filed: Jan. 4, 2002

(30) Foreign Application Priority Data

May 24, 2001 (KR) ......................................... 2001-28770

(51) Int. Cl.[7] ............................. A61K 7/42; A61K 7/44; A61K 7/00; A61K 35/78
(52) U.S. Cl. ........................... 424/59; 424/60; 424/400; 424/401; 424/725
(58) Field of Search ............................ 424/59, 60, 400, 424/401, 725

(56) References Cited

U.S. PATENT DOCUMENTS 4,288,433 A * 9/1981 Koulbanis et al.
4,525,359 A * 6/1985 Greenway, III et al.
5,612,038 A * 3/1997 Gedouin et al.

* cited by examiner

*Primary Examiner*—Shelley A. Dodson
(74) *Attorney, Agent, or Firm*—Birch, Stewart, Kolasch & Birch, LLP

(57) ABSTRACT

Disclosed is a UV blocking and slimming cosmetic composition containing laminaria water extract, octylmethoxycinnamate and oxybenzone.

5 Claims, No Drawings

UV BLOCKING AND SLIMMING COSMETIC COMPOSITION

TECHNICAL FIELD

The present invention relates to a cosmeceutical composition having both UV (ultraviolet) blocking and slimming effects. More specifically, the invention relates to the cosmetic composition having remarkably enhanced UV blocking and slimming effects without any harmful effects on the skin, containing laminaria water extract, octylmethoxycinnamate and oxybenzone.

BACKGROUND ART

Generally speaking, UV in the sunlight is classified into long-wavelength UV (UVA: 320–400 nm), medium-wavelength UV (UVB: 280–320 nm) and short-wavelength UV (UVC: 200–280 nm). Recently, the ozone layer becomes thinner and thinner due to the air pollution and in particular, has been severely disrupted in such an area as South Pole. Therefore, the human body has become to be exposed to more and more UV. Hitherto, UVC, extremely harmful to the human body, has been absorbed into the ozone layer and has reached the surface of the earth only at a negligible amount. Accordingly, UVA and UVB have been the main factors causing harmful effects on the skin. UVA has a tanning effect on the skin by formation of melanin and causes photo-toxicity, photo-allergy, etc. Medium-wavelength UV UVB, having a larger energy than UVA, causes sunburn (accompanying erythema or blister), skin cancer, pigmentation, denaturation of skin proteins, keratinization of skin cells, etc.

Therefore, a number of studies to develop cosmetics containing a UV blocking agent for the purpose of protecting the skin from harmful UV have been carried out. Hitherto, organic UV absorbents, such as octylmethoxycinnamate, butylmethoxydibenzoyl -methane, octyldimetyl PABA, cinnoxate, etc., have been used as UV absorbents. Inorganic pigments, such as titanium dioxide, ultrafine titanium dioxide particles, zinc oxide, ultrafine zinc oxide particles, talc, mica, kaolin, ferric oxide, etc., have been used as UV scattering agents. Organic UV absorbents have good absorption capability within a specific range of wavelength, but generally, have a narrower absorbable range of wavelength than inorganic UV scattering agents due to characteristics in the molecular structure. Therefore, it is required that organic UV absorbents having different ranges of the maximal absorption wavelength should be simultaneously used. In addition, because they are lipophilic and synthetic chemicals, they cause many kinds of harmful effects on the skin, particularly, allergies due to the light. For such reasons, organic UV absorbents are legally regulated as special materials and the quantity of use is regulated restricting the maximal content in cosmetics. Inorganic UV scattering agents have a UV blocking effect by scattering or reflecting UV. Accordingly, in case of using them solely, a sufficient UV blocking effect cannot be obtained due to the penetration of UV that has not been scattered or reflected. Moreover, in case of combining them in large quantities, cosmetics are likely to become coarse and the makeup looks unnatural. Particularly, ultrafine zinc oxide particles are good materials providing for the UV blocking effect and particularly, astringent and soothing, and wound healing effects on the skin irritated by the sunlight. However, in case of combining them with cosmetics at more than a specific amount, reaggregation occurs and leads to deteriorate the stability of cosmetics, for example, to disrupt emulsification. Therefore, their used amounts must be strictly regulated.

Generally, organic UV absorbents and inorganic UV scattering agents are simultaneously contained in UV blocking cosmetics to complement drawbacks from each other. However, because the content of each UV blocking agent is restricted, such a method cannot but have limit in solving the problems.

On the other hand, considerable kinds of cosmetics for slimming a particular part of the human body are currently commercialized. They contain natural substances derived from plants such as Boston ivy, caffeine, marronnier extracts, etc. For example, U.S. Pat. No. 4,525,359 discloses a slimming agent. In said patent, $\beta$-adrenergic agonists, preferably, theophylline, isoproterenol, forskolin, epinephrine, etc. are described as active agents for slimming. Also, U.S. Pat. No. 4,288,433 discloses the use of methylxanthine, particularly, caffeine and derivatives thereof, for providing the slimming effect.

However, slimming agents having been hitherto commercialized are not substantially effective. This is because the agents have been recommended being used in combination with other slimming programs or slimming diets. Especially, in U.S. Pat. No. 4,525,359, it is uncertain whether the weight reducing effect is derived from the slimming program or diet, or from the slimming agent.

DISCLOSURE OF THE INVENTION

The present inventors performed extensive studies to develop a new cosmeceutical composition having UV blocking and slimming effects. As a result, the inventors discovered that such cosmetic composition having both UV blocking and slimming effects could be obtained by combining laminaria water extract, octylmethoxycinnamate and oxybenzone in an appropriate ratio, and completed the present invention.

An object of the present invention is to provide a cosmetic composition having both UV blocking and slimming effects.

Another object of the present invention is to provide a process for preparing said cosmetic composition.

The present invention relates to a UV blocking and slimming cosmetic composition comprising laminaria water extract, octylmethoxycinnamate and oxybenzone.

In the present invention, the laminaria water extract is obtained by extracting laminaria with water under warming. Examples of laminaria employable in the present invention include Laminaria spp., for example, *L. japonica, L. ochotensis, L. religiosa,* etc.

The present composition may further contain one or more cosmetically acceptable carriers, auxiliaries and additives. That is, the composition contains laminaria water extract, octylmethoxycinnamate and oxybenzone as essential ingredients and may be manufactured into a conventional cosmetic formulation such as creams, lotions, solutions and suspensions by further containing one or more ingredients conventionally used in the manufacture of cosmetics.

In a preferable embodiment, the present composition contains 30 to 80% by weight of laminaria water extract, 3 to 10% by weight of octylmethoxycinnamate, and 1 to 5% by weight of oxybenzone. It may further contain one or more auxiliaries, diluents, preservatives, viscosity adjusting agents, antifoaming agents, cream bases, etc. in the amount of 30 to 80% by weight. The examples thereof include cetanol, stearyl alcohol, mineral oil, propylene glycol, white vaseline, polyoxyl stearate, Span #60, Tween #80

(polysorbate), methyl paraben, propyl paraben, sodium pyrosulfite, glycerin, ethanol, purified water, silicone resin or flavors, etc.

BEST MODE FOR CARRYING OUT THE INVENTION

This invention will be better understood from the following examples. However, one skilled in the art will readily appreciate the specific materials and results described are merely illustrative of, and are not intended to, nor should be intended to, limit the invention as described more fully in the claims which follows thereafter.

EXAMPLE 1
Preparation of a Cream

| | |
|---|---|
| Laminaria water extract | 50 g |
| Octylmethoxycinnamate | 6 g |
| Oxybenzone | 3 g |
| Cetanol | 4 g |
| Stearyl alcohol | 4 g |
| Mineral oil | 5 g |
| Propylene glycol | 10 g |
| White vaseline | 3 g |
| Polyoxyl stearate 40 | 3 g |
| Span #60 | 1 g |
| Tween #80 | 1 g |
| Methyl paraben | 180 mg |
| Propyl paraben | 20 mg |
| Sodium pyrosulfite | 1 g |
| Silicone resin | 1 g |
| Purified water | 7.8 g |
| Total | 100 g |

A cream was prepared using the above ingredients according to the preparation method disclosed in Korea Pharmacopoeia.

EXAMPLE 2
Preparation of a Solution

| | |
|---|---|
| Laminaria water extract | 50 g |
| Octylmethoxycinnamate | 6 g |
| Oxybenzone | 3 g |
| Tween #80 | 1 g |
| Methyl paraben | 180 mg |
| Propyl paraben | 20 mg |
| Sodium pyrosulfite | 1 g |
| Concentrated glycerin | 6 g |
| Ethanol | 20 g |
| Silicone resin | 1 g |
| Lemon flavor | q.s. |
| Purified water | residual |
| Total | 100 g |

A solution was prepared using the above ingredients according to the preparation method disclosed in Korea Pharmacopoeia.

Experiment 1: Skin Irritation Test

Using the product of the present invention and the commercial UV blocking agent, the skin irritation test was performed by the skin patch method as described below.

Materials: The cream prepared in Example 1 and SUN and INSECT protection (SPF 15) (Manufactured by Sharper Image, Lot No. 5300).

Subject: 40 females of the age of 18 to 50

Method: The subject females were divided into 2 groups (Group A and B), each of which consists of 20. To Group A was applied the Cream of Example 1 and to Group B was applied the commercial agent. The result is shown in the following Table 1.

TABLE 1

Skin irritation test of the product of Example 1 and the commercial agent

| Grades | Cream of Example 1 | Commercial Agent |
|---|---|---|
| +++ | 0 | 2 |
| ++ | 1 | 6 |
| + | 3 | 3 |
| ± | 8 | 5 |
| − | 8 | 4 |

+++: Strong trouble, ++: week trouble, +: very weak trouble, ±: normal, −: negative As can be seen from Table 1, in case of application of the commercial agent, 8 persons showed skin trouble and 3 persons showed very weak skin trouble. In comparison, in case of application of the Cream of Example 1, no one showed strong trouble and only one person showed weak trouble, and remaining persons were determined normal or negative.

Experiment 2: UV Blocking Test

Materials: Cream prepared in Example 1

Subject: 50 females of the age of 18 to 50

Method: The subject females were divided into 2 groups (Group A and B), each of which consists of 25. In Group A, UV irritation was carried out as follows after applying the Cream of Example 1. In Group B, UV irritation was carried out without applying any Cream. The skin having the diameter of 8 mm was irradiated by 70 mJ/cm$^2$ of UVB three times 1 week to artificially induce a tanning effect on the skin. A UV blocking effect in Group A was measured by Lab. Color. Mode. The measurement was repeated three times to obtain a mean value.

TABLE 2

Comparison of UV blocking effect after UV irradiation

| Group | Before irradiation | After 1 irradiation | After 2 irradiation | After 3 irradiation |
|---|---|---|---|---|
| A | 6.91 ± 2.64 | 7.23 ± 2.76 | 7.86 ± 3.26 | 8.61 ± 3.33 |
| B | 7.10 ± 3.02 | 8.02 ± 2.35 | 8.86 ± 3.23 | 12.76 ± 6.92 |

As shown in the above Table 2, the level of skin browning after 3 irradiations was increased by a total of 1.7 (about 24%) in Group A, whereas it was increased by a total of 5.66 (about 80%) in Group B. From these results, it was identified that the formulation of the present invention has excellent a UV blocking effect.

Experiment 3: Slimming Test

Material: Cream of Example 1 and Cream prepared by using the ingredients of Example 1 except laminaria water extract (Control cream)

Subject: Females of the age of 18 to 50 having topical obesity in thigh.

Method: The subject females were divided into two groups (Group A and B). To Group A was applied the Cream of Example 1 and to Group B applied the Control Cream. Before application of the Creams, the circumferences of both thighs as a standard were measured. In each group, the cream was applied only to one leg and used by squeezing a tube with a hand at an amount of about 5 cm each time. The creams were applied with sufficient massage to be equally absorbed into the skin with cellulite. The Creams were daily applied for 2 months. Then, the circumferences of both thighs were measured again and compared by an Image Analyzer. The result is shown in the following Table 3.

TABLE 3

Cellulite elimination effect

| Group | Before the use | After the use for 2 months | Change rate (%) |
|---|---|---|---|
| A | 17.51 | 15.86 | −9.6 |
| B | 17.22 | 17.25 | +0.2 |

As shown in the above Table 3, the Cream of the present invention had the slimming effect reducing thickness of the adipose layer about by 10% compared with that before the use.

INDUSTRIAL APPLICABILITY

As described above, the composition of the present invention has excellent UV blocking and slimming effects without any harmful effect on the skin.

What is claimed is:

1. A UV blocking and slimming cosmetic composition comprising laminaria water extract, octylmethoxycinnamate and oxybenzone.

2. The composition according to claim 1, comprising 30 to 80% by weight of laminaria extract, 3 to 10% by weight of octylmethoxycinnamate and 1 to 5% by weight of oxybenzone.

3. The composition according to claim 1, further comprising one or more cosmetically acceptable carriers, auxiliaries and additives.

4. The composition according to claim 3, comprising one or more cosmetically acceptable carriers, auxiliaries and additives in the amount of 30 to 80% by weight.

5. The composition according to claim 3, which is formulated into creams, lotions, solutions or suspensions.

* * * * *